United States Patent
Rice

(10) Patent No.: US 6,943,884 B2
(45) Date of Patent: Sep. 13, 2005

(54) LASER SYSTEM FOR DETECTION AND IDENTIFICATION OF CHEMICAL AND BIOLOGICAL AGENTS AND METHOD THEREFOR

(75) Inventor: Robert R. Rice, Simi Valley, CA (US)

(73) Assignee: The Boeing Company, Chicago, IL (US)

( * ) Notice: Subject to any disclaimer, the term of this patent is extended or adjusted under 35 U.S.C. 154(b) by 364 days.

(21) Appl. No.: 10/124,532

(22) Filed: Apr. 17, 2002

(65) Prior Publication Data

US 2003/0197860 A1 Oct. 23, 2003

(51) Int. Cl.$^7$ .............................................. G01N 21/61
(52) U.S. Cl. ...................................... 356/437; 250/343
(58) Field of Search .......................... 356/432, 436–439; 250/343

(56) References Cited

U.S. PATENT DOCUMENTS

| | | | |
|---|---|---|---|
| 3,788,742 A | * | 1/1974 | Garbuny .................... 356/5.03 |
| 5,298,751 A | * | 3/1994 | Fee et al. ................ 250/338.5 |
| 5,847,816 A | | 12/1998 | Zediker et al. |
| 5,847,817 A | | 12/1998 | Zediker et al. |
| 5,867,257 A | * | 2/1999 | Rice et al. ................. 356/28.5 |
| 6,128,081 A | * | 10/2000 | White et al. ................ 356/432 |
| 6,230,572 B1 | | 5/2001 | Pui et al. |

OTHER PUBLICATIONS

F. J. Duarte, Multiple–prism grating tunable laser oscillators: ultra–brief introduction, http://www.opticsjournal.com/tutorial.htm, Dec. 17, 1999.

* cited by examiner

*Primary Examiner*—Richard A. Rosenberger
(74) *Attorney, Agent, or Firm*—Harness Dickey & Pierce P.L.C.

(57) ABSTRACT

A micro-doppler ladar comprising a tunable laser to identify an unknown constituent of a gaseous cloud or region at a safe distance from the cloud or region. The tunable laser produces a laser beam tunable over a range of different frequencies. Each frequency produces a different vibrational response in the constituent in the gaseous cloud when the cloud or region is illuminated by the laser beam. A micro-doppler ladar system then interprets a back scattered beam to determine the induced vibrations. The determined induced vibrations can then be compared to known vibrations stored in a look-up table to identify the specific constituent(s) in the cloud or region.

21 Claims, 1 Drawing Sheet

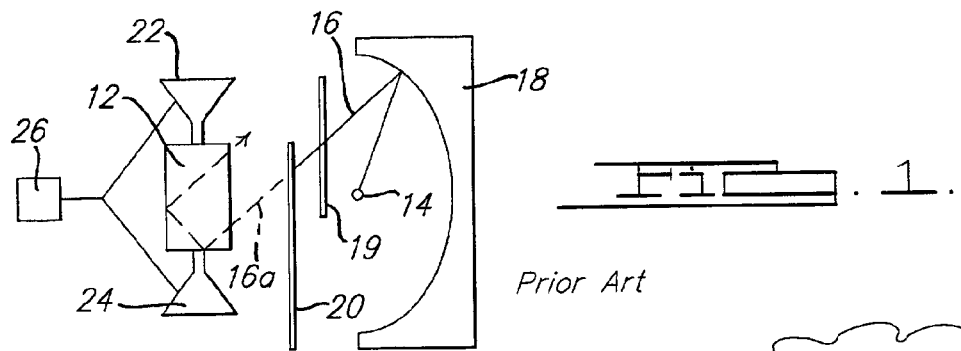
FIG. 1. Prior Art
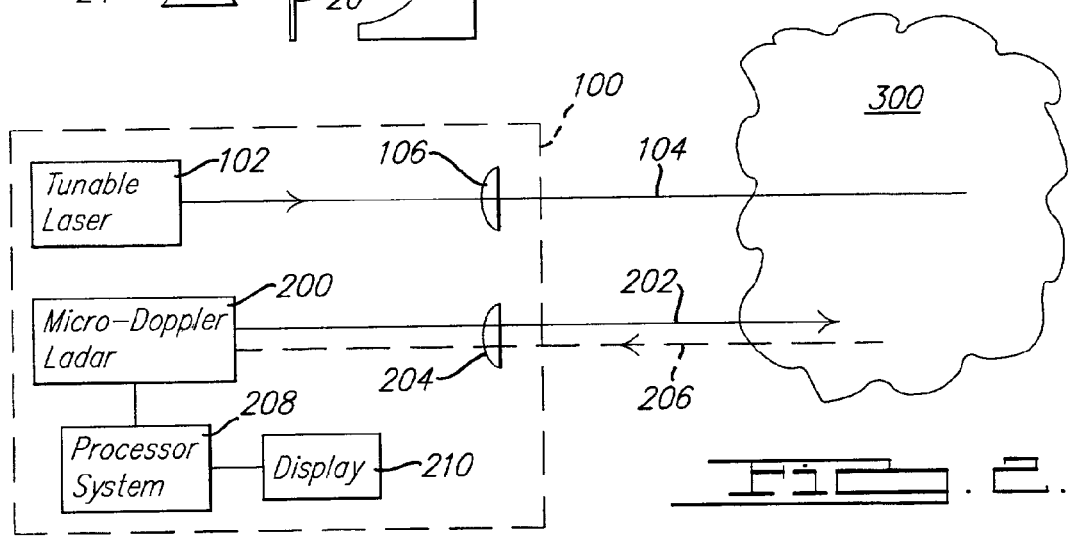
FIG. 2.
FIG. 3.

LASER SYSTEM FOR DETECTION AND IDENTIFICATION OF CHEMICAL AND BIOLOGICAL AGENTS AND METHOD THEREFOR

FIELD OF THE INVENTION

The present invention relates to standoff detection and identification of chemical and biological agents in a gaseous form, and more particularly to detection and identification of chemical and biological agents in a gaseous form from a standoff distance using a micro-doppler ladar system.

BACKGROUND OF THE INVENTION

It is often desirable to know the constituents or substances in a gaseous cloud from a distance before any personnel enter or venture near to the gaseous cloud. In particular, in modern times many chemical and biological agents, such as those for chemical and biological warfare, can be emitted into the atmosphere as a gaseous or amorphous cloud. When these substances are emitted into the atmosphere it is generally unknown what substances are present and what precautions must be taken. It is also desirable to know, also from a standoff distance, what substances might be present in a chemical plume such as from a chemical fire or spill. Though these are merely exemplary, it is understood that it is generally desirable to know the constituents and substances present in a gaseous cloud or region before any individual comes in contact with, or close proximity to, the cloud or region.

Though lab techniques for identifying different compounds and biological agents are generally well known in the art, doing such identification at a distance without confining the substance in any manner is often very difficult. Many times chemical spills, accidents, or even intentional acts, which release harmful chemical and biological agents into the atmosphere, are done well outside of controlled circumstances that allow for easy testing and identification of the chemical agents in the plume. It is desirable to identify unknown substances so that the personnel who must approach the plumes can take appropriate precautions.

One method uses raman back scattering spectroscopy. In this method, a monochromatic laser is pulsed through a cloud or region of suspicious gas. The internal vibrational characteristics of the molecules back scatter some of the photons without changing them if the photons match the vibrational characteristics of the molecules. The signals from a raman back scattering spectroscopy are generally very weak and therefore require that a very powerful laser be used for this purpose.

Other techniques such as Differential Absorption Lidar (DIAL) use infrared wavelengths to identify chemical species in a manner similar to conventional infrared absorption spectroscopy. An infrared laser beam is shined at a cloud or region of gas and light is reflected from the cloud. As the light is scattered back, different conditions act on the reflected light, such as range absorption of the suspicious region and atmosphere scattering, all allowing for the characterization of absorption lines to characterize the various chemical species present in the cloud or plume.

These systems, however, have inherent drawbacks such as requiring high powered lasers with very specific wavelength capabilities and highly absorbable infrared radiation. Many techniques that are generally used in the lab provide for highly specific characterizations of unknown molecules which these previously known methods and systems do not provide. One known technique can identify unknown gaseous molecules and even quantify the same photo acoustic spectroscopy (PAS). With reference to FIG. 1, a well-known PAS apparatus 10 is shown. The PAS apparatus 10 can be used to identify and quantify a gaseous substance which has been placed in a sample cell 12.

Briefly, PAS apparatus 10 works by providing a black body 14 which emits a ray 16 of infrared (IR) light. This IR light is focused by a mirror 18 towards the sample cell 12. A tuning source 19, such as a diffraction grading, limits the frequency of infrared light reaching the sample cell 12 at any given moment. Therefore, the frequency of infrared light reaching the sample cell 12 is known. The tuning apparatus 19 can tune the infrared ray of light 16 over a plurality of frequencies. A chopper 20 chops the ray of light 16 before it enters the sample cell 12. This produces an intermittent ray 16$a$ of light. The sample cell 12 includes a gaseous material which, when heated by a specific frequency of the ray 16$a$ of IR light, expands. Therefore, when the ray of light 16 is tuned to a specific frequency it will cause an expansion of the sample in the sample cell 12, if the sample absorbs that specific frequency of light. If the sample in the sample cell 12 expands, it will also then contract as that frequency of light is changed. This expansion and contraction of the sample cell produces a photo acoustic effect.

Microphones 22 and 24 detect the photo acoustic effect produced in the sample cell 12 and send the response to a processor 26. The processor 26 can then determine the identify of the sample that is present in the sample cell 12. The processor 26 knows the frequency of the ray of light 16 that reach the sample cell 12 to produce the photo acoustic effect at any given moment. Therefore, as each of a plurality of frequencies of light reach the sample cell 12, the processor 26 can create a spectrum for the sample in the sample cell 12. Comparing the spectrum to known spectrums, the processor 26 can then determine the identity of the sample in the sample cell 12. Quantification of the sample may also be performed due to the fact that the greater concentration of sample particles the greater the photo acoustic effect detected by the microphones 22, 24.

It would be highly desirable to be able to use such a system from a standoff distance to determine the substances in a gaseous cloud or region without enclosing that cloud or region in a sample cell. This would allow for determination of a gaseous substance from a distance without requiring high powered lasers or other devices.

SUMMARY OF THE INVENTION

The present invention is directed to a micro-doppler ladar comprising a tunable laser to identify an unknown constituent of a gaseous cloud or region. The tunable laser produces a laser beam tunable over a range of different frequencies. Each frequency produces a different vibrational response, creating a vibrational signature, in the constituent in the gaseous cloud. A micro-doppler ladar system then interprets a back scattered beam to determine the induced signature. The determined induced signature can then be compared to known signatures to identify the constituent in the cloud.

A first preferred embodiment of the present invention provides a apparatus to identify a substance in a gaseous cloud at a distance from the gaseous cloud. The apparatus comprises a laser which produces a laser beam tunable to one of a plurality of physical characteristics of laser light such that the substance in the gaseous cloud reacts. The apparatus also includes a micro-doppler system which receives a beam of light reflected back from the gaseous cloud, wherein the reflected beam includes a sample signature formed in the reflected beam produced by the reaction. A data storage device is used for storing known signatures of a plurality of substances. A processor then determines whether the sample signature substantially matches any of the stored known signatures. A display system is used to display the determination made by the processor.

A second preferred embodiment of the present invention comprises a ladar system for determining a constituent of a gas. The ladar system comprises a tunable laser beam tunable to a plurality of substantially discrete physical characteristics. The system further comprises a micro-doppler ladar system which senses a laser beam after the laser beam has been reflected from the constituent. The tunable laser beam provokes a plurality of discrete sample constituent characteristics in the constituent, wherein each discrete sample constituent characteristic is provoked by each discrete physical characteristic of the tunable laser beam. A processing system is incorporated into the system that comprises a memory system having a look-up table of a plurality of known constituent characteristics, and a processor. The processor can determine the constituent in the gas by comparing stored constituent characteristics in the look up table with the provoked response to find a match.

The present invention also provides for a new method of determining a constituent in a gaseous cloud from a safe distance. The method comprises providing a laser which is capable of producing a laser light beam which is tunable to a plurality of selectable physical characteristics. The laser light beam, comprising a selectable set of physical characteristics, is directed at a gaseous cloud including at least one unknown substance. The laser light beam produces a sample physical response in the substance due to the selectable set of physical characteristics. A look-up table of known physical responses and associated known substances is provided. Comparing the sample physical response to the look-up table of stored physical responses allows one to determine an identity of the substance in the gaseous cloud.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a diagrammatic view of a prior art photo-acoustic response spectroscopy system;

FIG. 2 is a diagrammatic view of a photo-accoustic micro-doppler ladar system according to a preferred embodiment of the present invention; and FIG. 3 is a detailed block diagram of the photo-accoustic micro-doppler ladar system in FIG. 2.

DETAILED DESCRIPTION OF THE PREFERRED EMBODIMENTS

The following description of the preferred embodiment(s) is merely exemplary in nature and is in no way intended to limit the invention, its application, or uses.

With reference to FIG. 2, a photo-accoustic micro-doppler ladar system 100 in accordance with a preferred embodiment of the present invention is shown. The system 100 is used to identify an unknown constituent, such as a chemical and biological species or substance, which is present in a gaseous cloud or area 300 from a safe distance.

The system 100 includes a tunable laser 102 which produces a tunable laser beam 104 having a plurality of selectable and discrete physical characteristics, such as a plurality of different and selectable wavelengths of light. The tunable laser beam 104 is focused through a lens 106 before the tunable laser beam 104 reaches the cloud 300. After reaching the cloud 300, a photo-accoustic response is created in the cloud 300. The system 100 also includes a micro-doppler ladar 200. The micro-doppler ladar 200 produces a highly coherent laser beam 202 which is also known as a sample laser beam, produced by a sample laser 212 (illustrated in FIG. 3). The sample laser beam 202 is focused through a lens 204 before the sample laser beam 202 reaches the cloud 300. The sample laser beam 202 is the sample retrieval laser beam. After the sample laser beam 202 has engaged the cloud 300, it reflected or back scattered and forms the backscattered or reflected laser beam 206. The back scattered laser beam 206 is reflected back through the focusing lens 204 to engage the micro-doppler ladar 200.

The reflected laser beam 206 is first processed in the micro-doppler ladar 200. A signal is generated by the micro-doppler ladar 200 which is interpreted by a processor system 208. Finally, a determination from the processor system 208 is sent to a display unit 210, via a signal, to be displayed. It will be understood that the display unit 210 may comprise any appropriate display unit. For example, the display unit 210 may include an LED display to indicate a safe or unsafe gaseous cloud 300, more complex CRT or LCD systems, which would give a description or probability of chemical and biological species present.

With reference to FIG. 3, the photo-accoustic micro-doppler ladar system 100 is illustrated in greater detail. The tunable laser 102 may be any appropriate tunable laser generally known in the art. As a brief description, not meant to be technically exhaustive, the tunable laser 102 generally includes a non-linear amplification material 116 which is pumped with a short wave laser or short wave radiation source 118. The short wave source 118 pumps the amplification material 116 which then emits a light beam including photons of two different wavelengths. The beam emitted by the amplification material 116 is the tunable laser beam 104. It will be understood, however, that the lens 106 may include prisms and gratings to columnate the emitted photons to increase the efficiency of the tunable laser beam 104. The energy of the two emitted photons is always equal to the energy of the pumping laser radiation source 118. The tunable laser beam 104 is then emitted through lens 106.

The tunable laser beam 104 is tuned by altering the amplification material 116. The amplification material may be any appropriate material or tunable parametric oscillator, such as lithium niobate ($LINBO_3$). Appropriate materials exhibit non-linear optical properties wherein a single photon will cause the emission of two others. It will be understood that other appropriate lasers include dye and diode lasers. The non-linear properties of the amplification material 116 allow that a change in orientation or temperature of the amplification material 116 will alter the frequencies of the two emitted photons. Therefore, altering or changing the temperature and/or orientation of the amplification material 116 allows the tunable laser beam 104 to be tuned to a plurality of frequencies. Also, by altering the amplification material 116 to a known temperature and orientation, a known frequency of light will be emitted from the amplification material 116. In this way, tunable laser beam 104 having a known frequency is produced.

The orientation and temperature of the amplification medium 116 is controlled by the processor system 208. Therefore, the signal received by the micro-doppler ladar 200 can be associated with a known frequency of the tunable laser beam 104.

The tunable laser beam 104 reaches the cloud 300 and heats a portion of the cloud 300. As the tunable laser beam 104 is tuned over a range of frequencies, different amounts of expansion will occur depending upon the constituent that is present in the cloud 300. Also, as the frequency of the tunable laser beam 104 changes from one frequency to the next, the response produced by the first frequency will change as the tunable laser beam 104 goes to the second frequency, thereby allowing a relaxation or condensation of the substance due to being illuminated at the first frequency. By tuning the tunable laser beam 104 from one frequency to another, the tunable laser beam 104 is effectively chopped. As described above in relation to the PAS apparatus 10, the vibrational response in the sample is induced by an expansion and contraction of the sample due to illumination by the intermittent beam. The constituents in the cloud 300, likewise, expand at a certain photon frequency and then contract as that photon frequency is eliminated. The constituents in the cloud 300 expand and contract creating a acoustic effect or vibration induced by the photons of the tunable laser beam 104, this is the photo acoustic effect. This photo acoustic effect creates a doppler effect in the reflected beam 206. The reflected beam 206 is then received by the micro-doppler ladar 200.

Once the tunable laser beam 104 has been used to excite and heat the gaseous cloud 300, so as to produce the photo acoustic effect, the reflected beam 206 is received by the micro-doppler ladar 200. The micro-doppler ladar 200 may be one similar to that described in U.S. Pat. No. 5,867,257 to Rice et al. entitled "Battlefield Personnel Threat Detection System and Operating Method Therefore", incorporated herein by reference. Generally, the micro-doppler ladar 200 comprises a laser 212 which produces the sample laser beam 202. The sample laser beam 202 reaches the cloud 300 and is then reflected back as reflected laser beam 206. The micro-doppler ladar 200 receives the reflected beam 206, which will be out of phase from the sample laser beam 202 depending upon the vibrations of the constituents in the cloud 300. The reflected beam 206 is received through the lens 204. FIG. 3 illustrates that both the sample laser beam 202 is emitted and the reflected beam 206 is received through a single lens 204. It will be understood, however, that the single lens 204 may be separated so that the sample beam 202 and the reflected beam 206 each have their own lens. It will be further understood that with the proper design, the lens 106, for the tunable laser beam 104, and the lens 204, for the micro-doppler ladar 200, may also be a single lens unit. The lens 204 focuses the reflected beam 206 as it enters the micro-doppler ladar 200. An amplification module 214 may be provided to amplify the reflected beam 206 to make the signature, as discussed herein, more easily detectable and to thereby facilitate analysis of the reflected beam.

The phase shift in the reflected beam 206 can be used to determine the velocity or vibration frequency produced in the gaseous cloud 300. As will be appreciated by those skilled in the art, the reflected beam 206 has a phase which varies due to the vibrations and distance of the cloud 300. This phase characteristic is the important characteristic which is relayed by the reflected beam 206 back to the system 100.

After reflected beam 206 has been amplified by the amplification module 214, the signal can be further processed if necessary. The processing of a reflected beam in a micro-doppler ladar 200 is well known in the art. One appropriate method and apparatus is discussed in U.S. Pat. No. 5,867,257 incorporated above. Briefly, the signal, produced by the amplifier 214, is communicated to the micro-doppler base band module 216 and to an integrator/low pass filter (I/LPF) 218. The micro-doppler base band module 216 determines the distance of the cloud 300 from the system 100. The vibrational characteristics of the constituents in the cloud 300 are determined in the I/LPF 218. The distance determined by the micro-doppler base band module 216 and the vibrational characteristics determined by the I/LPF 218 are then transferred to a processor 220 in the processor system 208.

The processor 220 then determines a sample "signature" for the constituent which is in the gaseous cloud 300. The processor 220 first determines the vibrational rate of the constituent in the cloud 300 for each of the frequencies of the tunable laser beam 104. Combining the vibrational rates for each frequency produces the signature for each of the constituents of the gaseous cloud 300 which is then compared to known signatures. The known signatures are stored in a memory core 220 in the processor system 208. The processor 220 then determines, within an appropriate confidence interval, the identity of the constituent of the gaseous cloud 300. It will be understood that the memory core 220 may also store the sample signatures so that the comparison need not occur in real time. That is, the comparison need not occur only as each vibrational rate of the sample signature is determined. Once the determination is made, the display unit 210 displays the identity of the constituents of the gaseous cloud 300.

Signatures for different constituents are created by inducing a different photo acoustic effect or a different magnitude of effect for each frequency of the tunable laser beam 104. The signature is a "graph" of a measurement of the photo acoustic effect at several photon wavelengths. If a laser other than tunable laser 102 were used, then the photo acoustic effect would be singular. Simply, a non-tunable laser would provoke only one photo acoustic effect for each constituent. It is likely, however, that more than one constituent would have an identical photo acoustic effect for any given photon frequency of the laser beam. Therefore, since the tunable laser beam 104 is produced by a tunable laser 102, a different photo acoustic effect can be induced for each frequency of the tunable laser beam 104. This plurality of unique photo acoustic effects provides a signature or fingerprint for each constituent. It is unlikely that any two constituents will have an identical or substantially similar signature. In addition, only known harmful chemicals or biological agents need be stored in the memory core 220. Furthermore, the signatures can be limited to only a few predetermined photon frequencies. These predetermined frequencies can be selected for scanning. Thus, only the predetermined frequencies must be produced by the tunable laser 102 in the tunable laser beam 104. This will reduce the number of frequencies that must be processed by the processor 220 to only those necessary to provide an appropriate confidence level to identify different constituents.

Using the present invention allows identification of unknown chemical and/or biological constituents in a cloud or plume from a safe standoff distance. It will be understood, however, that any appropriate tunable laser and micro-doppler system may be used in the present invention. It will also be understood that various tunable lasers using different amplification materials 116 can be used depending upon the possible constituent(s) of the gaseous cloud 300. For example, biological constituents, such as anthrax spores, are more likely to produce photo acoustic effects with an ultra-violet laser. However, organic compounds, such as nerve gases, are more likely to produce photo acoustic effects with mid to long wavelength infrared light. Finally, nuclear weapons or nuclear material will emit or create iodine isotopes, such as $1^{131}$, that may be determined by creating a photo acoustic effect with a tunable laser 102 tuned through a very narrow bandwidth. Therefore, a micro-doppler ladar system 100 may include one or more than one tunable laser 102 to produce more than one tunable laser beam 104, depending upon the range of detection desired or necessary. Therefore, the description of a micro-doppler ladar system 100 with only a single tunable laser 102 is not meant to limit the scope of the present a invention.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An apparatus to identify a substance in a gaseous cloud at distance from the gaseous cloud, the apparatus comprising:

a tunable laser which produces a laser beam tunable to one of a plurality of physical characteristics of laser light such that the substance in the gaseous cloud reacts when illuminated by the laser beam;

a micro-doppler system which receives a beam of light reflected back from the gaseous cloud;

a sample signature formed in said reflected beam produced by said reaction;

a data storage device for storing known signatures of a plurality of different substances;

a processor for comparing said sample signature with said known signatures and determining whether said sample signature substantially matches any one of said stored known signatures; and a display system to display a determination made by said processor as to whether said substance in said gaseous cloud comprises one of said different substances corresponding to said known signatures.

2. The apparatus of claim 1, wherein said physical characteristics of laser light comprise a frequency of said laser light; and wherein said tunable laser beam selectively comprises a specific selected frequency at a given instant.

3. The apparatus of claim 1, wherein said tunable laser beam is tunable between at least a first frequency and a second frequency.

4. The apparatus of claim 3, wherein said first frequency invokes a first expansion of the substance and said second frequency invokes a second expansion of the substance, and wherein the substance contracts after each expansion.

5. The apparatus of claim 4, wherein said expansions and said contractions produce vibrations which produce said sample signature which is compared to said known signature.

6. The apparatus of claim 5, further comprising:

a sample laser which produces a sample laser beam;

wherein said sample laser beam produces said reflected beam; and wherein said reflected beam transfers the sample signature to said micro-doppler system from the substance.

7. The apparatus of claim 1, wherein said processor compares said sample signature and said known signatures to produce a confidence interval of a match between said sample signature and one of said known signatures, wherein said processor compares a predetermined number of peaks in said known signature to said sample signature, wherein the greater number of peaks that match the higher confidence interval.

8. A micro-doppler ladar system for determining a constituent of a gas remotely from the gas, the micro-doppler ladar system comprising:

a tunable laser for generating a tunable laser beam tunable to a plurality of substantially discrete physical characteristics;

a sample laser which produces a sample laser beam;

a doppler system that senses said sample laser beam after said sample laser beam has been directed at the gas and reflected from the gas;

a processing system comprising a memory system and a processor;

wherein said tunable laser beam provokes a plurality of discrete sample constituent characteristics in the constituent, and wherein each said discrete sample constituent characteristic is provoked by each said discrete physical characteristic of said tunable laser beam;

wherein said memory system comprises a look-up table including a stored plurality of known constituent characteristics; and wherein said processor determines the constituent in the gas by comparing said discrete sample constituent characteristics with said known constituent characteristics to determine a match therebetween.

9. The micro-doppler ladar system of claim 8, wherein said sample constituent characteristic comprises a vibration due to an expansion and contraction of the constituent.

10. The micro-doppler ladar system of claim 9, wherein said doppler system measures a doppler effect in said reflected sample laser beam from the constituent due to said vibration.

11. The micro-doppler ladar system of claim 8, wherein said memory system also stores sample constituent characteristics to be compared with stored sample constituents in said look-up table, so that said comparison does not occur in real time.

12. The micro-doppler ladar system of claim 8, wherein said sample constituent characteristics and said known constituent characteristics comprise vibration signatures induced by discrete physical characteristics of said tunable laser beam.

13. The micro-doppler ladar system of claim 8, wherein said tunable laser comprises a tunable parametric oscillator.

14. The micro-doppler ladar system of claim 8, wherein said substantially discrete physical characteristic comprises a photon of a particular wavelength.

15. A method of detecting a substance in a gaseous cloud remotely from the cloud, the method comprising:

providing a laser which is capable of producing a laser light beam which is tunable to a plurality of selectable physical characteristics;

directing said laser light beam, comprising at least one physical characteristic of a selectable set of physical characteristics, at said gaseous cloud including said substance;

measuring a physical response in said substance due to said one physical characteristic; and determining an identity of said substance in said gaseous cloud by comparing said sample physical response to known physical responses that comprise known expansion and contraction responses associated with a known substance.

16. The method of claim 15, further comprising:

pulsing said laser light beam, wherein each said pulse of said beam comprises a distinct selectable set of physical characteristics, at said gaseous cloud including said at least one substance;

producing a plurality of physical responses in said substance due to said pulsed laser light beam;

comparing said plurality of physical responses to said look-up table; and determining an identity of said substance in said gaseous cloud based upon said plurality of physical characteristics.

17. The method of claim 15, wherein each of said selectable set of physical characteristics comprises a substantially discrete wavelength of light.

18. The method of claim 15, further comprising:

providing a sample laser which is capable of producing a coherent sample laser beam;

directing said sample laser beam at said gaseous cloud including said substance;

using said sample laser beam to detect said sample physical response in said substance due to said one physical characteristic; and measuring said detected one physical characteristic.

19. The method of claim 15, further comprising:

providing a look-up table of known physical responses and associated known substances.

20. A method of detecting a substance in a gaseous cloud remotely from the cloud, the method comprising:

providing a laser which is capable of producing a laser light beam which is tunable to a plurality of selectable physical characteristics;

directing said laser light beam, comprising at least one physical characteristic of a selectable set of physical characteristics, at said gaseous cloud including said substance;

measuring a physical response in said substance due to said one physical characteristic;

providing a look-up table of known physical responses and associated known substances;

and determining an identity of said substance in said gaseous cloud by comparing said sample physical response to said look-up table of said known physical responses;

wherein said sample physical response comprises an expansion and contraction pattern substantially unique to the substance in the gaseous cloud.

21. A method of detecting a substance in a gaseous cloud remotely from the cloud, the method comprising:

providing a laser which is capable of producing a laser light beam which is tunable to a plurality of selectable physical characteristics;

directing said laser light beam, comprising at least one physical characteristic of a selectable set of physical characteristics, at said gaseous cloud including said substance;

measuring a physical response in said substance due to said one physical characteristic;

determining an identity of said substance in said gaseous cloud based at least in part on the measured physical response;

wherein said sample physical response comprises an expansion and contraction pattern substantially unique to the substance in the gaseous cloud.

* * * * *